(12) United States Patent
Kumagai et al.

(10) Patent No.: US 6,376,752 B1
(45) Date of Patent: Apr. 23, 2002

(54) CYTOPLASMIC INHIBITION OF GENE EXPRESSION IN A PLANT

(75) Inventors: Monto H. Kumagai, Davis; Guy R. Della-Cioppa, Vacaville; Jonathan Donson, Oak Park; Damon A. Harvey, Berkeley; Laurence K. Grill, Vacaville, all of CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 09/436,068

(22) Filed: Nov. 8, 1999

Related U.S. Application Data (60) Division of application No. 09/265,576, filed on Mar. 9, 1999, which is a continuation of application No. 08/260,546, filed on Jun. 16, 1994, now Pat. No. 5,922,602, which is a continuation-in-part of application No. 08/184,237, filed on Jan. 19, 1994, now Pat. No. 5,589,367, which is a continuation of application No. 07/923,692, filed on Jul. 31, 1992, now Pat. No. 5,316,931, which is a continuation-in-part of application No. 07/600,244, filed on Oct. 22, 1990, now abandoned, application No. 09/436,068, which is a continuation-in-part of application No. 07/739,143, filed on Aug. 1, 1991, now abandoned, and a continuation-in-part of application No. 07/737,899, filed on Jul. 26, 1991, now abandoned, and a continuation-in-part of application No. 07/641,617, filed on Jan. 16, 1991, now abandoned, said application No. 07/600,244, is a continuation of application No. 07/310,881, filed on Feb. 17, 1989, now abandoned, which is a continuation-in-part of application No. 07/160,766, filed on Feb. 26, 1988, now abandoned, and a continuation of application No. 07/160,771, filed on Feb. 26, 1988, now abandoned, said application No. 07/641,617, is a continuation of application No. 07/347,637, filed on May 5, 1989, said application No. 07/737,899, is a continuation of application No. 07/363,138, filed on Jun. 8, 1989, now abandoned, which is a continuation-in-part of application No. 07/219,279, filed on Jul. 15, 1988, now abandoned.

(51) Int. Cl.[7] ............................ A01H 5/00; A01H 1/00; A01H 7/00; A01H 9/00; A01H 11/00

(52) U.S. Cl. ......................... 800/295; 800/285; 800/286
(58) Field of Search ....................... 435/320.1; 800/295, 800/285, 286

(56) References Cited

U.S. PATENT DOCUMENTS 5,316,930 A * 5/1994 Loesch-Fries et al. ...... 800/280

OTHER PUBLICATIONS

French et al, Science, vol. 231: pp. 1294–1297, Mar. 1986.*

* cited by examiner

*Primary Examiner*—Terry McKelvey
(74) *Attorney, Agent, or Firm*—Albert P. Halluin; Thomas Gallegos; Viola T. Kung (57) ABSTRACT

The invention provides novel genetic constructions for the expression of inhibitory RNA in the cytoplasm of eukaryotic cells. The inhibitory RNA may be an anti-sense RNA or a co-suppressor RNA, and functions to reduce the expression of a gene of interest in the target cell. The genetic constructions of the invention are capable of replicating in the cytoplasm of a eukaryotic cell and comprise a promoter region in functional combination with an encoding polynucleotide. The genetic constructions may be designed so as to replicate in the cytoplasm of plant cells, yeast cells, and mammalian cells. When the eukaryotic cell of interest is a plant cell, the genetic construction is preferably derived from a plant RNA virus. Plant RNA virus derived genetic constructions may employ a plant virus subgenomic promoter, including subgenomic promoters from tobamoviruses in functional combination with the RNA encoding region. In a preferred embodiment of the invention, plant cells are induced to produce elevated levels of the carotenoid phytoene. The elevated levels of phytoene are achieved by inhibiting the expression of the enzyme phytoene desaturase using the vectors of the invention.

9 Claims, 2 Drawing Sheets

FIGURE 1

| | | |
|---|---|---|
| PDS-Nb | ATAAACCCTGACGAGCTTTCGATGCAGTGCATCTTGATTGCTTTGAACAG | 50 |
| | ||||||||||||||| ||||| |||||||||||| ||||| || ||||||| | |
| PDS-Le | ATAAACCCTGACGAACTTTCAATGCAGTGCATTTTGATCGCATTGAACAG | 50 |
| PDS-Nb | ATTTCTTCAGGAGAAACATGGTTCAAAAATGGCCTTTTTAGATGGTAACC | 100 |
| | |||||||||||||||||||||||||||||||||||||||||||||||| | | |
| PDS-Le | GTTTCTTCAGGAGAAACATGGTTCAAAAATGGCCTTTTTAGATGGTAATC | 100 |
| PDS-Nb | CTCCTGAGAGACTTTGCATGCCGATTGTGGAACATATTGAGTCAAAAGGT | 150 |
| | |||||||||||||||||||||||||||| ||||| |||||||||||||| | |
| PDS-Le | CTCCTGAGAGACTTTGCATGCCGATTGTTGAACACATTGAGTCAAAAGGT | 150 |
| PDS-Nb | GGCCAAGTCAGACTAAACTCACGAATAAAAAAGATCGAGCTGAATGAGGA | 200 |
| | ||||||||||||| ||||||||||||||||||||| ||||||||||||| | |
| PDS-Le | GGCCAAGTCAGACTGAACTCACGAATAAAAAAGATTGAGCTGAATGAGGA | 200 |
| PDS-Nb | TGGAAGTGTCAAATGTTTTATACAGAATAATGGCAGTACAATTAAAGGAG | 250 |
| | |||||||||||| ||||| ||| || | || ||| |||| | |||| | |
| PDS-Le | TGGAAGTGTCAAGAGTTTTATACTGAGTGACGGTAGTGCAATCGAGGGAG | 250 |
| PDS-Nb | ATGCTTTTGTGTTTGCCACTCCAGTGGATATCTTGAAGCTTCTTTTGCCT | 300 |
| | |||||||||||||||| ||||||||||||| || ||||||||| |||||| | |
| PDS-Le | ATGCTTTTGTGTTTGCCGCTCCAGTGGATATTTTCAAGCTTCTATTGCCT | 300 |
| PDS-Nb | GAAGACTGGAAAGAGATCCCATATTTCCAAAAGTTGGAGAAGCTAGTGGG | 350 |
| | |||||||||||||||||| |||||||||||||||||||||||||| |||| || | |
| PDS-Le | GAAGACTGGAAAGAGATTCCATATTTCCAAAAGTTGGAGAAGTTAGTCGG | 350 |
| PDS-Nb | AGTTCCTGTGATAAATGTCCATATATGGTT | 380 |
| | ||| |||||||||||||| |||||||||| | |
| PDS-Le | AGTACCTGTGATAAATGTACATATATGGTT | 380 |

SEQUENCE LISTING

<160> NUMBER OF SEQ ID NOS: 15

<210> SEQ ID NO 1
<211> LENGTH: 26
<212> TYPE: DNA
<213> ORGANISM: Tomato mosaic virus

<400> SEQUENCE: 1
ctcgcaaagt ttcgaaccaa atcctc 26

<210> SEQ ID NO 2
<211> LENGTH: 35
<212> TYPE: DNA
<213> ORGANISM: Tomato mosaic virus

<400> SEQUENCE: 2
cggggtacct gggccccaac cgggggttcc ggggg 35

<210> SEQ ID NO 3
<211> LENGTH: 41
<212> TYPE: DNA
<213> ORGANISM: Tomato mosaic virus

<400> SEQUENCE: 3
tcctcgagcc taggctcgca aagtttcgaa ccaaatcctc a 41

<210> SEQ ID NO 4
<211> LENGTH: 24
<212> TYPE: DNA
<213> ORGANISM: Tomato mosaic virus

<400> SEQUENCE: 4
tatgtatggt gcagaagaac agat 24

<210> SEQ ID NO 5
<211> LENGTH: 25
<212> TYPE: DNA
<213> ORGANISM: Tomato mosaic virus

<400> SEQUENCE: 5
agtcgactct tcctcttctg gcatc 25

<210> SEQ ID NO 6
<211> LENGTH: 30
<212> TYPE: DNA
<213> ORGANISM: Tomato mosaic virus

```
<400> SEQUENCE: 6
tgctcgagtg tgttcttcag ttttctgtca                                    30

<210> SEQ ID NO 7
<211> LENGTH: 25
<212> TYPE: DNA
<213> ORGANISM: Tomato mosaic virus

<400> SEQUENCE: 7
aactcgagcg ctttctccga agctt                                         25

<210> SEQ ID NO 8
<211> LENGTH: 20
<212> TYPE: DNA
<213> ORGANISM: Tomato mosaic virus

<400> SEQUENCE: 8
ggcactcaac tttataaacc                                               20

<210> SEQ ID NO 9
<211> LENGTH: 20
<212> TYPE: DNA
<213> ORGANISM: Tomato mosaic virus

<400> SEQUENCE: 9
cttcagtttt ctgtcaaacc                                               20

<210> SEQ ID NO 10
<211> LENGTH: 25
<212> TYPE: DNA
<213> ORGANISM: Nicotiana benthamiana

<400> SEQUENCE: 10
taatcgatga tgattcggag gctac                                         25

<210> SEQ ID NO 11
<211> LENGTH: 20
<212> TYPE: DNA
<213> ORGANISM: Nicotiana benthamiana

<400> SEQUENCE: 11
ctcctttaat tgtactgcca                                               20

<210> SEQ ID NO 12
<211> LENGTH: 114
<212> TYPE: DNA
<213> ORGANISM: Tomato mosaic virus
<220> FEATURE:
<221> NAME/KEY: CDS
<222> LOCATION: (28)...(114)

<400> SEQUENCE: 12
gttttaaata cgctcgaggt tttaaat atg tct gtt gcc ttg tta tgg gtt gtt   54
                             Met Ser Val Ala Leu Leu Trp Val Val
                              1               5 tct cct tgt gac gtc tca aat ggg aca agt ttc atg gaa tca gtc cgg   102
Ser Pro Cys Asp Val Ser Asn Gly Thr Ser Phe Met Glu Ser Val Arg
 10                  15                  20                  25 gag gga aac cgt                                                    114
Glu Gly Asn Arg

<210> SEQ ID NO 13
```

```
<211> LENGTH: 29
<212> TYPE: PRT
<213> ORGANISM: Tomato mosaic virus

<400> SEQUENCE: 13

Met Ser Val Ala Leu Leu Trp Val Val Ser Pro Cys Asp Val Ser Asn
  1               5                  10                  15

Gly Thr Ser Phe Met Glu Ser Val Arg Glu Gly Asn Arg
             20                  25

<210> SEQ ID NO 14
<211> LENGTH: 380
<212> TYPE: DNA
<213> ORGANISM: Nicotiana benthamiana

<400> SEQUENCE: 14
ataaaccctg acgagctttc gatgcagtgc atcttgattg ctttgaacag atttcttcag    60
gagaaacatg gttcaaaaat ggcctttta gatggtaacc ctcctgagag actttgcatg   120
ccgattgtgg aacatattga gtcaaaaggt ggccaagtca gactaaactc acgaataaaa   180
aagatcgagc tgaatgagga tggaagtgtc aaatgtttta tacagaataa tggcagtaca   240
attaaaggag atgcttttgt gtttgccact ccagtggata tcttgaagct tcttttgcct   300
gaagactgga aagagatccc atatttccaa aagttggaga agctagtggg agttcctgtg   360
ataaatgtcc atatatggtt                                               380

<210> SEQ ID NO 15
<211> LENGTH: 380
<212> TYPE: DNA
<213> ORGANISM: Tomato phytoene desaturase (PDS-Le)

<400> SEQUENCE: 15
ataaaccctg acgaactttc aatgcagtgc attttgatcg cattgaacag gtttcttcag    60
gagaaacatg gttcaaaaat ggccttttta gatggtaatc ctcctgagag actttgcatg   120
ccgattgttg aacacattga gtcaaaaggt ggccaagtca gactgaactc acgaataaaa   180
aagattgagc tgaatgagga tggaagtgtc aagagtttta tactgagtga cggtagtgca   240
atcgagggag atgcttttgt gtttgccgct ccagtggata ttttcaagct tctattgcct   300
gaagactgga aagagattcc atatttccaa aagttggaga agttagtcgg agtacctgtg   360
ataaatgtac atatatggtt                                               380
```

CYTOPLASMIC INHIBITION OF GENE EXPRESSION IN A PLANT

This application is a divisional application of U.S. patent application Ser. No. 09/265,576, filed Mar. 9, 1999; which is a continuation of U.S. patent application Ser. No. Ser. No. 08/260,546, filed Jun. 16, 1994, now U.S. Pat. No. 5,922, 602; which is a Continuation-in-Part of Ser. No. 08/184,237, filed Jan. 19, 1994, U.S. Pat. No. 5,589,367; which is a Continuation of Ser. No. 07/923,692, filed Jul. 31, 1992, now U.S. Pat. No. 5,316,931; which is a Continuation-in-Part of Ser. No. 07/600,244, filed Oct. 22, 1990, now abandoned; and a Continuation-in-Part of Ser. No. 07/641, 617, filed Jan. 16, 1991, now abandoned; and a Continuation-in-Part of Ser. No. 07/737,899, filed Jul. 26, 1991, now abandoned; and a Continuation-in-Part of Ser. No. 07/739,143, file Aug. 1, 1991, now abandoned; said 07/600,244 is a Continuation of Ser. No. 07/310,881, file Feb. 17, 1989, now abandoned; which is a Continuation-in-Part of Ser. No. 07/160,766, filed Feb. 26, 1988, now abandoned; and a Continuation in part of 07/160,771, filed Feb. 26, 1988, now abandoned; said Ser. No. 07/641,617, is a Continuation of Ser. No. 07/347,637, filed May 5, 1989, now abandoned; said Ser. No. 07/737,899, is a Continuation of Ser. No. 07/363,138, Jun. 8, 1989, now abandoned; which is a Continuation-in-Part of Ser. No. 07/219,279, filed Jul. 15, 1988, now abandoned.

FIELD OF THE INVENTION

This invention is in the field of gene regulation through anti-sense RNA endogenously produced inhibitory RNA molecules such as anti-sense RNA and co-suppressor RNA.

BACKGROUND

One of the primary goals of genetic engineering has been to control the expression of selected genes in eukaryotic organisms of interest. While it has been relatively straight-forward to insert new genes for expression into eukaryotic cells, the targeting of endogenous genes for reduced expression has been more difficult to achieve. Site-directed inactivation of genes in higher organisms has required extremely complex genetic manipulations and is not applicable to a wide range of organisms. One method of reducing the expression of specific genes in eukaryotic organisms has been through the use of anti-sense RNA and through co-suppression.

Anti-sense RNA has been used to reduce the expression of pre-selected genes in both plants and animals. Descriptions of the use of anti-sense RNA to reduce the expression of selected genes in plants can be found, among other places in U.S. Pat. No. 5,107,065, Smith et al., *Nature* 334:724–726 (1988), Van der Krol et al., *Nature* 333:866–869 (1988), Rothstein et al., *Proc. Natl. Acad. Sci. USA* 84:8439–8443 (1987), Bird et al., *Bio/Technology* 9:635–639 (1991), Bartley et al., *Biol. Chem.* 267:5036–5039 (1992), and Gray et al., *Plant Mol. Bio.* 19:69–87 (1992).

Another method of reducing the expression of specific genes in eukaryotic organisms is through the use of co-suppressor RNA. Co-suppressor RNA, in contrast to anti-sense RNA, is in the same orientation as the RNA transcribed from the target gene, i.e., the "sense" orientation.

It is possible that biochemical pathways in plants transfected with hybrid viruses could be altered by overproducing an enzyme involved in a rate-limiting step, or by inhibiting the synthesis of an enzyme via antisense RNA. Although the expression of numerous genes in transgenic plants have been repressed by antisense RNA, the actual mechanism and location of inhibition is not known. In the nucleus, antisense RNA may directly interfere with transcription or form duplexes with the heterogeneous nuclear (hnRNA). There is evidence that inhibition of endogenous genes can occur in transgenic plants containing sense RNA, A. R. van der Krol et al., *Nature* 333:866–869 (1988) and C. Napoli et al., *Plant Cell* 2:279–289 (1990). Mechanism of this down regulation or "co-suppression" is thought to be caused by the production of antisense RNA by read through transcription from distal promoters located on the opposite strand of the chromosomal DNA (Greison, et al. *Trends in Biotech.* 9:122–123 (1991)). Alternatively, in the cytoplasm, antisense RNA may form a double-stranded molecule with the complimentary mRNA and prevent the translation of mRNA into protein.

Tobamoviruses, whose genomes consist of one plus-sense RNA strand of approximately 6.4 kb, replicate solely in the cytoplasm, and can be used as episomal RNA vectors to alter plant biochemical pathways. Hybrid tobacco mosaic (TMV)/odontoglosum ringspot viruses (ORSV) have been used previously to express heterologous enzymes in transfected plants (Donson, et al., *Proc. Natl. Acad. Sci. USA* 88:7204 (1991) and Kumagai, et al., *Proc. Natl. Acad. Sci. USA* 90:427–430 (1993), minus-Sense RNA Strand (Miller, et al.). Infectious RNA transcripts from viral cDNA clones encode proteins involved in RNA replication, movement, and encapsidation (10). Subgenomic RNA for messenger RNA synthesis is controlled by internal promoters located on the minus-sense RNA strand (*N. benthamiana* plants were inoculated with in vitro transcripts as described previously [W. O. Dawson, et al., *Proc. Natl. Acad. Sci. USA* 83:1832 (1986)]). Insertion of foreign genes into a specific location under the control of an additional subgenomic RNA promoter have resulted in systemic and stable expression of neomycin phosphotransferase and α-trichosanthin (Donson, et al., *Proc. Natl. Acad. Sci. USA* 88:7204 (1991) and Kumagai, et al., *Proc. Natl. Acad. Sci. USA* 90:427–430 (1993)).

One of the many biochemical pathways that could serve as a target for genetic manipulation is the biosynthesis of carotenoids. On the first committed step in carotenoid biosynthesis in higher plants is the condensation of two geranylgeranyl pyrophosphate molecules to phytoene, a colorless $C_{40}$ hydrocarbon, by the enzyme phytoene synthase. In the ripening fruit of *Lycopersicon esculentum*, phytoene synthase is a monomeric, chloroplast localized protein with an approximate relative molecular mass of 42 kDa. This enzyme is initially synthesized as a 47-kDa preprotein and is processed by the removal of a transit peptide during import to the chloroplast (Bartley, et al., *J. Biol. Chem.* 267:5036–5039 (1992)). Transgenic tomato plants containing anti-sense to phytoene synthase mRNA produce yellow fruit and pale flowers. Although the fruit specific carotenes are reduced by 97%, the levels of carotenoids in the leaves of the transgenic plants are unaffected, (Bird, et al., *Bio/Technology* 9:635–639 (1991)). It has been proposed that an additional set of biosynthetic genes occurs in plants which regulate the expression of leaf specific carotenoids.

The subsequent step in the biosynthetic pathway is the modification of the colorless phytoene to phytofluene and ζ-carotene by phytoene desaturase. Among higher plants, the isolation of gene encoding this enzyme has been described for tomato, Pecker, et al., *Proc. Natl. Acad. Sci. USA*, 89:4962 (1992), and *Arabidopsis thaliana* (Scolnick and Bartley, *Plant Physiol.* 103:147 (1993)). Phytoene desaturase is inhibited by norflurazon, a bleaching herbicide, in a reversible, non-competitive manner (Sandman, et al., *Target Sites of Herbicide Actions*, G. Sandman, P. Boger Es. (RC press, Boca Rotan (1989)). Application of this compound causes a dramatic decrease in leaf carotenoids and chlorophylls and a subsequent accumulation of phytoene. The reduction of the photoprotective carotenoids derived from phytoene may cause a rapid destruction of chlorophyll by photooxidation.

The need for new methods of reducing the expression of specific genes in eukaryotes is clearly established. The invention described herein provides new methods for reducing the expression of selected genes, genetic constructions for practicing the methods, and cells transformed by these genetic constructions, and higher organisms comprising the transformed cells.

SUMMARY OF THE INVENTION

One aspect of the invention is to provide novel genetic constructions for the expression of inhibitory RNA in the cytoplasm of eukaryotic cells. The genetic constructions of the invention are capable of replicating in the cytoplasm of a eukaryotic cell and comprise a promoter region in functional combination with an inhibitory RNA encoding polynucleotide, i.e., encoding an anti-sense RNA or a co-suppressor RNA. The genetic constructions of the invention may be designed so as to replicate in the cytoplasm of plant cells, yeast cells, or mammalian cells. When the eukaryotic cell of interest is a plant cell, the genetic construction is preferably derived from a plant RNA virus, more preferably a positive single-stranded RNA virus. Plant RNA virus derived genetic constructions may comprise a plant virus subgenomic promoter, including subgenomic promoters from tobamoviruses, in functional combination with the inhibitory RNA encoding region.

Another aspect of the invention is to provide cells comprising the genetic constructions of the invention and to provide organisms comprising a plurality of such cells.

Another aspect of the invention is to provide methods of reducing the expression of a gene of interest in eukaryotic cells, i.e., methods of producing eukaryotic cells exhibiting reduced levels of expression of a gene of interest. The methods of the invention comprise the step of transforming a cell with a genetic construction of the invention in which the inhibitory RNA encoding region is specific for the gene of interest. Another aspect of the invention is to provide plant cells that produce elevated levels of the carotenoid phytoene. The elevated levels of phytoene are achieved by inhibiting the expression at the enzyme phytoene desaturase using the vectors of the invention.

BRIEF DESCRIPTION OF THE FIGURES

FIG. 1. Phytoene expression vector TTO1/PSY+. This plasmid contains the TMV-U1 126-, 183-, and 30-kDa ORFs, the ToMV coat protein gene (ToMVcp), the SP6 promoter, the tomato phytoene synthase gene, and part of the pBR322 plasmid. The TAA stop codon in the 30-kDa ORF is underlined. The TMV-U1 subgenomic promoter located within the minus strand of the 30-kDa ORF controls the expression of phytoene synthase. The putative transcription start point (tsp) of the subgenomic RNA is indicated with a period (.). A portion of the N terminal amino acid sequence of phytoene synthase (SEQ ID NO: 12) is given. The DNA sequence encoding this portion of the plasmid is also given (SEQ ID NO: 13).

FIG. 2. Nucleotide sequence comparison of *N. benthamiana* leaf phytoene desaturase (PDS1-Ab) (SEQ ID NO: 14) and tomato phytoene desaturase (PDS-Le) (SEQ ID NO: 15). The nucleotides are aligned to maximize sequence similarity.

DESCRIPTION OF THE SPECIFIC EMBODIMENTS

Definitions

The term "inhibitory RNA", as used herein, refers to an RNA molecule that interferes with the expression of a target gene. An "inhibitory RNA" is specific for one or more target genes. An inhibitory RNA may be an anti-sense RNA with respect to an RNA molecule transcribed from the target gene. Alternatively, the target gene inhibitory RNA may be a co-suppressor RNA with respect to an RNA molecule transcribed from the target gene.

The term "anti-sense RNA" as used herein, refers to an RNA molecule that is capable of forming a duplex with a second RNA molecule. Thus a given RNA molecule is said to be an anti-sense RNA molecule with respect to a second, complementary or partially complementary RNA molecule, i.e., the target molecule. An anti-sense RNA molecule may be complementary to a translated or an untranslated region of a target RNA molecule. The anti-sense RNA need not be perfectly complementary to the target RNA. Anti-sense RNA may or may not be the same length of the target molecule; the anti-sense RNA molecule may be either longer or shorter than the target molecule.

The term "co-suppressor RNA" refers to an RNA molecule that effects suppression of expression of a target gene where the RNA is partially homologous to an RNA molecule transcribed from the target gene. A co-suppressor RNA molecule is the RNA molecule that effects co-suppression as described in U.S. Pat. No. 5,231,020, Krol et al., *Biotechniques* 6:958–976 (1988), Mol et al., *FEBS Lett.* 268:427430 (1990), and Grierson, et al., *Trends in Biotech.* 9:122–123 (1991) and similar publications. A "co-suppressor" RNA is in the sense orientation with respect to the target gene, i.e., the opposite orientation of the anti-sense orientation.

The term "inhibitory RNA encoding polynucleotide" as used herein, refers to a polynucleotide, e.g., DNA, RNA, and the like, capable of being transcribed, when in functional combination with a promoter, so as to produce an inhibitory RNA molecule, e.g., an anti-sense RNA or a co-supressor RNA. Anti-sense RNA encoding polynucleotides and co-supressor encoding polynucleotides are both embodiments of the inhibitory RNA encoding polynucleotides. When the inhibitory RNA is an anti-sense RNA, the inhibitory RNA transcribed from the inhibitory RNA encoding polynucleotide region of the genetic constructions of the invention is preferably perfectly complementary to the entire length of the RNA molecule or molecules for which the anti-sense RNA is specific, i.e., the target. The anti-sense RNA encoding polynucleotide in the subject vectors may encode an anti-sense RNA that forms a duplex with a non-translated region of an RNA transcript such as an intron region, or 5' untranslated region, a 3' untranslated region, and the like. Similarly, a co-suppressor encoding polynucleotide in the subject vectors may encode an RNA that is homologous to translated or untranslated portions of a target RNA. An anti-sense RNA encoding polynucleotides may be conveniently produced by using the non-coding strand, or a portion thereof, of a DNA sequence encoding a protein of interest.

The term "reduced expression," as used herein, is a relative term that refers to the level of expression of a given gene in a cell produced or modified by the claimed methods as compared with a comparable unmodified cell, i.e., a cell lacking the subject vector, under a similar set of environmental conditions. Thus, a cell modified by the subject methods, i.e., a cell having "reduced expression" of the gene of interest, may express higher levels of that gene under a first set of environmental conditions, than a comparable unmodified cell under a second set of environmental conditions, if the second set of conditions is highly favorable to gene expression.

The Invention

The invention described herein exploits the discovery that RNA can reduce the expression of a target gene through inhibitory RNA interactions with target mRNA that take place in the cytoplasm of a eukaryotic cell, rather than in the nucleus. Prior to the invention, it was not known if inhibitory RNA reduced gene expression by means of an interaction that takes place in the cytoplasm or an interaction that takes place in the nucleus. Thus, prior to the invention, it was necessary to produce inhibitory RNA in the nucleus so as to be certain that inhibition would be achieved. Furthermore, it was not known if adequate concentrations of inhibitory RNA could be provided in the cytoplasm. Cytoplasmic expression of inhibitory RNA (specific for target genes) has numerous advantages over nuclear expression, these advantages include the ability to use high level expression vectors that are not suitable for nuclear expression. The use of such vectors is particularly advantageous in plants, because vectors capable of systemically infecting plants may be used to produce the inhibitory RNA. The invention described herein has many aspects. These aspects include novel genetic constructions for the expression of target gene inhibitory RNA in the cytoplasm of eukaryotic cells, cells transfected with these genetic constructions, multicellular organisms comprising the transfected cells, and methods for reducing the expression of selected genes in a cell by transforming a cell with a genetic construction of the invention.

There are numerous ways to produce the genetic constructions of the invention. Techniques for manipulating polynucleotides, e.g., restriction endonuclease digestion and ligation, are well known to a person of ordinary skill in the art. These conventional polynucleotide manipulation techniques may be used to produce and use the genetic construction of the invention. While some optimization of standard techniques may be employed to produce the subject genetic constructions, significant experimentation is not required to produce the genetic constructions or practice the claimed methods.

The genetic constructions of the invention comprise a promoter region in functional combination with an inhibitory RNA encoding polynucleotide. The promoter region is selected so as to be capable of driving the transcription of a polynucleotide sequence in a host cell of interest. Thus for example, when the eukaryotic cell is a plant cell, the promoter is selected so as to be able to drive transcription in plant cells. Promoters capable of functioning in a given eukaryotic cell are well known to a person of ordinary skill in the art. Examples of promoters capable of driving transcription in a cell of interest can be found, among other places in, Goeddel et al., *Gene Expression Technology Methods in Enzymology* Volume 185, Academic Press, San Diego (1991), Ausubel et al., *Protocols in Molecular Biology*, Wiley Interscience (1994), and similar publications. When the cell for transformation is a plant cell, the RNA virus subgenomic promoters are preferably used as promoter regions. RNA virus subgenomic promoter are described, among other places in Dawson and Lehto, *Advances in Virus Research*, 38:307–342, PCT published application WO 93/03161.

The genetic constructions of the invention are capable of replication or maintenance, at least transiently, in the cytoplasm of eukaryotic cells of interest i.e., a base vector. Thus, the genetic constructions of the invention necessarily comprise a polynucleotide region derived from a vector capable of being replicated or stably maintained in eukaryotic cell of interest. Many vectors capable of replication (or stable maintenance) in different types of eukaryotic cells are known. For example, vectors for use in yeast cells include $2\mu$ circle derived vectors. Information describing vectors yeast and their use in yeast can be found, among other places, in Goeddel, et al. supra, Ausubel et al., supra, and similar publications.

Vectors for use in mammalian cells include bovine papilloma virus derived vectors, vaccinia derived vectors, semiliki forrest virus vectors and the like. Information describing mammalian cell vectors and their use in mammalian cells can be found, among other places is Goeddel, et al. supra, and Ausubel et al., supra. Vectors for use in plants include vectors derived from cauliflower mosaic virus, tobacco mosaic virus, tomato mosaic virus, and the like. Information describing plant cell vectors and their use in plant cells can be found, among other places, in PCT published application WO 93/03161, and Donson, et al., *Proc. Natl. Acad. Sci. USA* 88:7204–7208 (1991).

The promoter driving transcription of the inhibitory RNA encoding region of the subject genetic constructions may be selected so as have a level of transcriptional activity sufficient to achieve the desired degree of expression of the target gene inhibitory RNA of interest. The promoter may be native or heterologous to the cell for genetic modification. The promoter may also be native or heterologous to the base vector, i.e., the portion of the vector other than the promoter and the inhibitory RNA encoding region. The promoter may be inducible or constitutive. Preferably, strong promoters are used to drive transcription of the inhibitory RNA encoding polynucleotide when the target RNA is highly expressed.

The invention also provides methods of reducing the expression of a gene or genes of interest in a eukaryotic cell. As a consequence of providing the subject methods of reducing gene expression in eukaryotic cell, the subject invention also provides methods of producing a eukaryotic cell having reduced expression of a gene of interest and eukaryotic cells that have reduced expression of a gene of interest, as produced by the methods of the invention. Reduction of gene expression is achieved by introducing one or more of the vectors of the invention into a eukaryotic cell. The vector used to transform the cell of interest comprises an inhibitory RNA encoding polynucleotide that encodes an inhibitory RNA specific for the gene for which reduced expression is sought. The method of reducing expression of the gene of interest comprises the step of introducing the subject genetic vector into a host cell that is capable of expressing the gene of interest under certain environmental conditions. The vector may be introduced into a cell of interest by any of a variety of well known transformation methods. Such methods include: infection, transfection, electroporation, ballistic projectile transformation, conjugation, and the like. The inventive aspect of the subject methods is not dependent upon the particular means by which the inhibitory RNA encoding vector is introduced into the cell of interest. The particular methods of introducing the vector into a cell of interest is, in part, dependent upon the particular cell for modification and the precise type of vector selected.

When the eukaryotic cells of interest for genetic modification by the subject vectors are plant cells, the vectors are preferably derived from RNA plant viruses. Preferred RNA plant virus vectors are positive strand single stranded RNA viruses. RNA plant virus vectors may be conveniently manipulated and introduced into cells in a DNA form instead of working directly with RNA vectors. Viral vector derived from tobamoviruses are particularly preferred. Descriptions of suitable plant virus vectors that may be modified so as to contain an inhibitory RNA encoding region in functional combination with a promoter as well as how to make and use such vectors, can be found in, among other places, PCT publication number WO 93/03161, Kumagai et al., *Proc. Natl. Acad. Sci. USA* 90:427–430 (1993).

The invention also provides polynucleotides encoding phytoene synthase and phytoene desaturase, as well as various vector for the expression of target gene inhibitory RNA specific for phytoene synthase genes or phytoene desaturase genes. The first committed step in carotenoid biosynthesis in higher plants is the condensation of two geranylgeranyl pyrophosphate molecules to phytoene, a colorless $C_{40}$ hydrocarbon, by the enzyme phytoene synthase. The subsequent step in the biosynthetic pathway is the modification of the colorless phytoene to phytofluene and ζ-carotene by phytoene desaturase.

The invention provides polynucleotides encoding the phytoene desaturase enzyme from Nicotiana species and numerous derivatives thereof. Specifically, the invention provides, in purified form, polynucleotides encoding the phytoene desaturase of *Nicotiana benthamiana*. Additionally, the invention provides polynucleotides encoding tomato (*Lycopersicon esculentum*) phytoene synthase and phytoene desaturase. The phytoene synthase and phytoene desaturase encoding polynucleotides described herein may be used to produce inhibitory RNAs specific for phytoene synthase and phytoene desaturase genes from a variety of plant species. The phytoene synthase and phytoene desaturase inhibitory RNA are preferably produced by transcription of phytoene synthase or phytoene desaturase inhibitory RNA encoding polynucleotides in functional combination with a promoter region.

The amino acid sequence of the various phytoene desaturase and the phytoene synthase enzymes described herein and the naturally occurring polynucleotide sequences encoding these enzymes enable a person of ordinary skill in the art of molecular biology to design and construct a variety of related molecules having useful properties similar to these enzymes and the polynucleotides obtained directly from the cloning of the cDNAs encoding these enzymes. In the case of polynucleotides, the degeneracy of the genetic code permits the person of ordinary skill in the art to produce numerous different polynucleotides encoding the same polypeptide, i.e., isocoding polynucleotides. The precise polynucleotide sequence produced may be selected so as to optimize expression in a particular host cell type, taking into account factors affecting expression such as codon frequency, potential mRNA secondary structures, methylation, and the like. The invention also provides a variety of polypeptides having the same enzymatic activity as phytoene desaturase and phytoene synthase, but differing in one or more amino acid residues, so as to produce a phytoene desaturase and phytoene synthase variant polypeptides. Variant polypeptides may be produced and designed in a wide variety of ways. Phytoene desaturase and phytoene synthase variants may be produced and designed by introducing mutations (either random or by design) into a polynucleotide sequence encoding the enzyme, transforming the mutated enzyme encoding polynucleotide (operably linked to a suitable promoter) into a host cell, and subsequently assaying the host cell for the expression of the desired enzymatic activity. The identity of mutations in Srf I encoding polynucleotides introduced randomly, may be determined by sequencing the polynucleotide encoding the enzyme.

The invention also provides for the recombinant DNA expression of phytoene desaturase and phytoene synthase (as well as variants thereof). The recombinant expression of these enzyme may be achieved through standard recombinant DNA expression technology. Suitable recombinant DNA expression technology can be found, among other places, in Goeddel, et al., *Gene Expression Technology: Methods in Enymology Volume* 185 Academic Press, San Diego (1991). The enzyme may be expressed in a wide range of host cells, including both eukaryotic and prokaryotic host cells. One advantage of providing the subject enzymes by recombinant DNA methodology is the production of increased amounts of enzyme from reduced amounts of cellular material.

Another advantage of the recombinant production of the enzymes is the ability to produce the enzyme free of certain contaminants. Phytoene synthase and phytoene desaturase (and variants thereof) produced by recombinant DNA techniques may be purified by procedures similar to the procedures described herein for the purification of the non-recombinant enzyme. Guidance in devising and modifying enzyme purification procedures can be found, among other places in Deutscher, *Guide to Protein Purification Methods in Enzymology—Volume* 182, Academic Press, San Diego (1990), Scopes *Protein Purification: Principles and Practice*, 3rd edition, Springer-Verlag, N.Y. (1993), and the like.

The invention may be better understood by referring to the following examples. The following examples are offered for the purpose of illustrating the invention and should not be interpreted as a limitation of the invention.

EXAMPLES

Example 1

Isolation of Tomato Mosaic Virus cDNA

An 861 bp fragment (5524–6384) from the tomato mosaic virus (fruit necrosis strain F; ToMV-F) containing the putative coat protein subgenomic promoter, coat protein gene, and the 3' end was isolated by PCR using ToMV primers 5' CTCGCAAAGTTTCGAACCAAATCCTC 3' (SEQ ID NO: 1) (upstream) and 5'CGGGGTACCTGGGCCCCAAC-CGGGGGTTCCGGGGG3' (SEQ ID NO: 2) (downstream) and subcloned into the HincII site of pBluescript KS–. A hybrid virus consisting of TMV-U1 and ToMV-F was constructed by swapping an 874-bp XhoI-KpnI ToMV fragment into pBGC152 (Kumagai, et al., *Proc. Natl. Acad. Sci. USA* 90:427–430 (1993)), creating plasmid TTO1. The inserted fragment was verified by dideoxynucleotide sequencing. A unique AvrII site was inserted downstream of the XhoI site in TTO1 by PCR mutagenesis, creating plasmid TTO1A, using the following oligonucleotides:

5' TCCTCGAGCCTAGGCTCGCAAAGTTTC-GAACCAAATCCTCA 3' (SEQ ID NO: 3) (upstream),

5' CGGGGTACCTGGGCCCCAACCGGGGGT-TCCGGGGG 3' (SEQ ID NO: 2) (downstream).

Example 2

Isolation of a cDNA Encoding Tomato Phytoene Synthase and a Partial cDNA Encoding Tomato Phytoene Desaturase Partial cDNAs were isolated from ripening tomato fruit RNA by polymerase chain reaction (PCR) using the following oligonucleotides: PSY, 5' TATGTATGGTGCAGAA-GAACAGAT 3' (SEQ ID NO:4) (upstream), 5' AGTC-GACTCTTCCTCTTCTGGCATC 3' (SEQ ID NO: 5) (downstream); PDS, 5' TGCTCGAGTGTGTTCT-TCAGTTTTCTGTCA 3' (SEQ ID NO: 6) (upstream), 5' AACTCGAGCGCTTTGATTTCTCCGAAGCTT 3' (SEQ ID NO: 7) (downstream). Approximately 3×10$^4$ colonies from a Lycopersicon esculentum cDNA library were screened by colony hybridization using a 32 P labelled tomato phytoene synthase PCR product. Hybridization was carried out at 42° C. for 48 h in 50% formamide, 5×SSC, 0.02 M phosphate buffer, 5×Denhart's solution, and 0.1 mg/ml sheared calf thymus DNA. Filters were washed at 65° C. in 0.1×SSC, 0.1% SDS prior to autoradiography. PCR products and the phyoene synthase cDNA clones were verified by dideoxynucleotide sequencing.

Example 3

DNA Seguencing and Computer Analysis.

A 1.2 Kb PstI, BamHI fragment containing the phytoene synthase cDNA and a 0.7 Kb the partial phytoene desaturase cDNA was subcloned into pBluescript KS+(Stratagene, La Jolla, Calif.). The nucleotide sequencing of KS+/PDS #38 and KS+5'3'PSY was carried out by dideoxy termination using single stranded templates. Nucleotide sequence analysis and amino acid sequence comparisons were performed using PCGENE and DNA Inspector IIE programs.

Example 4

Construction of the Tomato Phytoene Synthase Expression Vector

Figure 1:
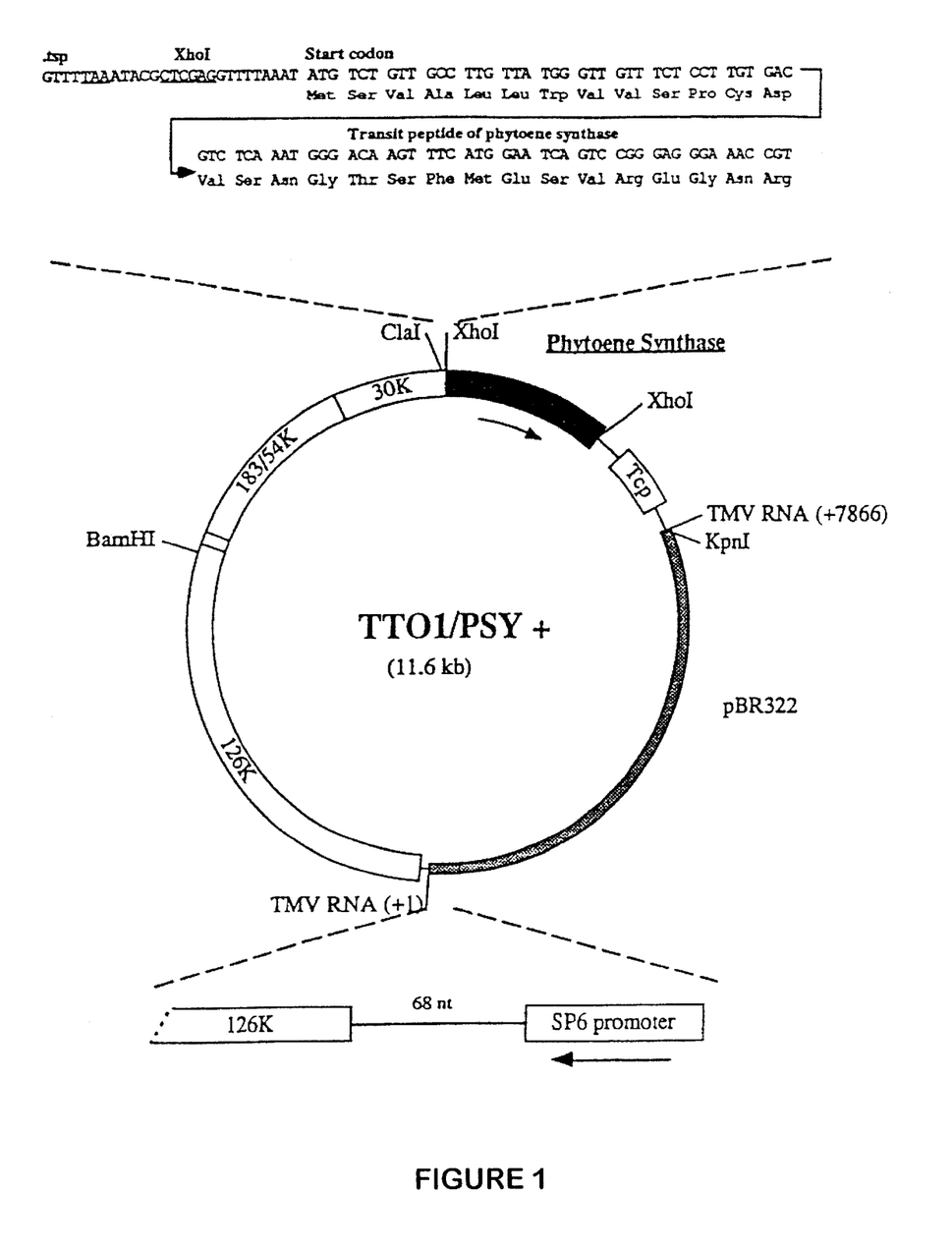

A 1253 base pair XhoI fragment containing the tomato phytoene synthase cDNA was subcloned into TTO1. The vector TTO1/PSY+ (FIG. 1) contains the phytoene synthase cDNA (positive orientation) under the control of the TMV-U1 coat protein subgenomic promoter; while, the vector TTO1/PSY- contains the phytoene synthase cDNA in the anti-sense orientation.

Example 5

Construction of a Viral Vector Containing a Partial Tomato Phytoene Destaturase cDNA An XhoI fragment containing the partial tomato phytoene desaturase cDNA was subcloned into TTO1. The vector TTO1A/PDS+ contains the phytoene desaturase cDNA (positive orientation) under the control of the TMV-U1 coat protein subgenomic promoter; while, the vector TTO1/PDS- contains the phytoene desaturase cDNA in the anti-sense orientation.

A partial cDNA encoding phytoene desaturase was isolated from N. benthamiana leaf RNA by RT-PCR using the following oligonucleotides: PDS, 5' GGCACTCAACTT-TATAAACC 3' (SEQ ID NO: 8) (upstream), 5' CTTCAGTTTTCTGTCAAACC 3' (SEQ ID NO: 9) (downstream) and verified by dideoxynucleotide sequencing.

Example 6

Transfection and Analysis of N. Benthamiana [TTO1/PSY+, TTO1/PSY, TTO1/PDS700+, TTO1/PDS700-]

Infectious RNAs from TTO1/PSY+ (FIG. 1), TTO1/PSY-, TTO1A/PDS+, TTO1/PDS- were prepared by in vitro transcription using SP6 DNA-dependent RNA polymerase and were used to mechanically inoculate N. benthamiana (Dawson, et al., Adv. Virus Res. 38:307 (1990)). The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. Plants transfected with TTO1/PSY+ showed at least a two fold increase in phytoene synthase activity over plants transfected with viral vector controls. Leaves from systemically infected TTO1/PSY+ plants developed a bright orange phenotype and accumulated high levels of phytoene (Table 1). The leaves and sepals from TTO1/PDS- plants developed a white bleaching phenotype similar to that seen with the herbicide norflurazon. The structure of the chloroplasts from TTO1/PSY+ and TTO1/PDS- transfected plants, when analyzed by transmission electron microscopy, appeared to be normal. Leaves from systemically infected TTO1A/PDS+ plants developed a bleaching white phenotype approximately one week later than leaves from anti-sense TTO1/PDS- plants and also accumulated high levels of phytoene.

Agarose gel electrophoresis of PCR cDNA isolated from virion RNA and Northern blot analysis of virion RNA indicate that the vectors are maintained in an extrachromosomal state and have not undergone any detectable intramolecular rearrangements.

TABLE I

Quantitation of phytoene leaves of N. benthamiana transfected with viral transcripts.

| Plant | Phytoene µg/g FW | fold increase |
|---|---|---|
| N. benthamiana | 4.6 | 1 |
| N. benthamiana: TTO1/PDS- | 234.8 | 51.0 |
| N. benthamiana: Norflurozon | 339.8 | 73.9 |
| N. benthamiana: TTO1/PSY+ | 52.4 | 11.4 |
| N. benthamiana: TTO1/PSY- | 1.0 | 0.2 |

Example 7

Purification and Analysis of Phytoene from Transfected Plants

Phytoene was extracted in methanol and identified by its peak retention time and absorption spectra on a 25-cm Spherisorb ODS-1 5-µm column using acetonitrile/methanol/2-propanol (85:10:5) as a developing solvent at a flow rate of 1 ml/min. The phytoene isolated from systemically infected tissue had an identical retention time to phytoene from norflurozon treated plants. The phytoene peak from N. benthamiana transfected with TTO1/PSY+ had a characteristic optical absorbance maxima at 276, 285, and 298 nm. One week after inoculation, plants transfected with viral encoded phytoene synthase showed a hundredfold increase in phytoene compared to the levels in noninfected plants as measured by HPLL separation of carotenoids. The carotenoids were extracted in methanol and identified by their peak retention time and absorption spectra on a 25-cm Spherisorb ODS-1 5-µm column using acetonitrile/methanol/2-propanol (85:10:5) as a developing solvent. The expression of sense (TTO1A/PDS+) and anti-sense (TTO1/PDS-) RNA to a partial phytoene desaturase in transfected plants inhibited the synthesis of colored carotenoids and caused the systemically infected leaves to develop a white phenotype. HPLC analysis of these plants revealed that they also accumulated phytoene high levels. The bleaching of leaves was reproduced in control plants treated with the herbicide norflurozon, a non-competitive inhibitor of phytoene desaturase.

Example 8

Isolation of a Partial cDNA Encoding N. Benthamiana Phytoene Desaturase

A partial cDNA clone that encodes for N. benthamiana phytoene desaturase was isolated from young leaf tissue. Nucleotide sequence comparison of 369 bp in the corresponding regions between tomato and N. benthamiana phytoene desaturase indicate that they are 92% similar to each other (FIG. 2). Since the two plant genes have areas of high homology, cytoplasmic inhibition of the endogenous plant gene by viral-derived antisense RNA may occur through the formation of hybrid, double stranded RNA molecules. The down regulation of phytoene desaturase in plants transfected with TTO1A/PDS+ may be caused by direct interference during the translation of mRNA into protein or by duplexes formed between mRNA and viral-derived negative strand RNA, although the precise mechanism of action does not need to be known to carry out the invention.

Example 9

Construction of TTO1 and TTO1A Expression Vectors

An 861 bp fragment (5524–6384) from the tomato mosaic virus (fruit necrosis strain F; ToMV-F) containing the putative coat protein subgenomic promoter, coat protein gene, and the 3' end was isolated by PCR using ToMV primers 5' CTCGCAAAGTTTCGAACCAAATCCTC 3' (SEQ ID NO: 1) (upstream) and 5' CGGGGTACCTGGGCCCCAAC-CGGGGGTTCCGGGGG 3' (SEQ ID NO: 2) (downstream) and subcloned into the HincII site of pBluescript KS–. A hybrid virus consisting of TMV-U1 and ToMV-F was constructed by swapping an 874-bp XhoI-KpnI ToMV fragment into pBGC152 (I. Pecker, et al., *Proc. Natl. Acad. Sci. USA* 89:4962 (1992)), creating plasmid TTO1. The inserted fragment was verified by dideoxynucleotide sequencing. A unique AvrII site was inserted downstream of the XhoI site in TTO1 by PCR mutagenesis, creating plasmid TTO1A, using the following oligonucleotides:

5' TCCTCGAGCCTAGGCTCGCAAAGTTTCGAACCAAATCCTCA 3' (upstream) (SEQ ID NO: 3),

5' CGGGGTACCTGGGCCCCAACCGGGGGTTCCGGGGG 3' (SEQ ID NO: 2) (downstream).

Example 10

Construction of TTO1/PDS−. TTO1A/PDS+

Using PCR mutagenesis a XhoI fragment, encoding tomato phyotene synthase was amplified from a *Lycopersicon esculentum* cDNA clone isolated from a ripening fruit cDNA library, and placed under the control of the TMV-U1 coat protein subgenomic promoter by subcloning into TTO1.

Example 11

Inhibition of the Expression of a Specific Endogenous Plant Gene (Phytoene Desaturase) Using an RNA Viral Vector: Transfection and Analysis of *N. Benthamiana* [TTO1/PDS−, TTO1A/PDS+

Infectious RNAs from TTO1A/PDS+, TTO1/PDS− were prepared by in vitro transcription using SP6 DNA-dependent RNA polymerase and were used to mechanically inoculate *N. benthamiana*. The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. The leaves and sepals from TTO1/PDS− plants developed a white bleaching phenotype similar to that seen with the herbicide norflurazon. The structure of the chloroplasts from TTO1/PDS− transfected plants, when analyzed by transmission electron microscopy, appeared to be normal. Leaves from systemically infected TTO1A/PDS+ plants developed a bleaching white phenotype approximately one week later than leaves from antisense TTO1/PDS plants and also accumulated high levels of phytoene.

Example 12

Inhibition of the Expression of a Specific Endogenous Plant Gene (Phytoene Synthase) Using an RNA Viral Vector: Transfection and Analysis of *N. Benthamiana*[TTO1/PSY−]

Infectious RNAs from TTO1/PSY− were prepared by in vitro transcription using SP6 DNA-dependent RNA polymerase and were used to mechanically inoculate *N. benthamiana*. The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. Plants transfected with TTO1/PSY+ showed at least a two fold increase in phytoene synthase activity over plants transfected with viral vector controls (data not shown). Leaves from systemically infected TTO1/PSY+ plants developed a bright orange phenotype and accumulated high levels of phytoene (Table 1). The leaves from TTO1/PDS− plants developed a light bleaching phenotype. The structure of the chloroplasts from TTO1/PSY− when analyzed by transmission electron microscopy, appeared to be normal. Leaves from systemically infected TTO1A/PSY− plants did not accumulate phytoene.

Example 13

Isolation of a Partial cDNA Encoding *N. Benthamiana* Phytoene Desaturase

A partial cDNA clone that encodes for *N. benthamiana* phytoene desaturase was isolated from young leaf tissue. Nucleotide sequence comparison of 380 bp in the corresponding regions between tomato and *N. benthamiana* phytoene desaturase indicate that they are 92% similar to each other (FIG. 2). Since the two plant genes have areas of high homology, cytoplasmic inhibition of the endogenous plant gene by viral-derived antisense RNA may occur through the formation of hybrid, double stranded RNA molecules. The down regulation of phytoene desaturase in plants transfected with TTO1A/PDS+ may be caused by direct interference during the translation of mRNA into protein or by duplexes formed between mRNA and viral-derived negative strand RNA.

Example 15

Analysis of PDS mRNA in Nicotina Cells Producing Tomato PDS Derived Specific Anti-sense RNA Reverse Transcriptase PCR experiments measuring the presence or absence of detectable PDS mRNA transcripts in N. benthamiana cells containing TTO1/PDS− (producing PDS anti-sense RNA) were performed. RNA was isolated from transfected plants by the method of Gailiano et al. The primers used to detect TTO1/*L. esculeutum* were 5' TAATC-GATGATGATTCGGAGGCTAC3' (SEQ ID NO 10) (upstream) 5' GGCACTCAACTTTATAAACC3' (SEQ ID NO: 8) (downstream). The primer used to detect *N. benthamiana* transcripts were 5' GGCACTCAACTT-TATAAACC3' (SEQ ID NO: 8) (upstream) and 5' CTCCTT-TAATTGTACTGCCA3' (SEQ ID NO: 11) (downstream). The PCR experiments were unable to detect endogenous PDS mRNA in the vector transfected plants, while the expected 452 bp anti-sense transcript could be detected. The 219 bp PDS mRNA could only be detected in the control, non-infected, *N. benthamiana plants.*

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A plant comprising a plurality of plant cells having a reduced expression of a target gene, wherein said plant cells are produced by a method comprising the steps of transfecting a cell with a viral vector capable of replication in the cytoplasm of a eukaryotic cell, wherein said viral vector comprises a first subgenomic promoter in functional combination with a polynucleotide which encodes a target gene inhibitor RNA, wherein said viral vector further comprises a second subgenomic promoter operably linked to a viral coat protein encoding polynucleotide.

2. A plant according to claim 1, wherein said first or second subgenomic promoter is a plant viral RNA subgenomic promoter.

3. A plant according to claim 1, wherein at least one of said subgenomic promoters is derived from a tobamovirus.

4. The plant according to claim 1, wherein said target gene is an endogenous plant gene.

5. The plant according to claim 1, wherein said target gene inhibitor RNA is an anti-sense RNA.

6. The plant according to claim 1, wherein said target gene inhibitor RNA is a co-suppressor RNA.

7. The plant according to claim 1, wherein said viral vector is obtained from a positive single-stranded RNA virus.

8. The plant according to claim 7, wherein said positive single-stranded RNA virus is a tobamovirus.

9. The plant according to claim 8, wherein said tobamovirus is a tobacco mosaic virus.

* * * * *